(12) United States Patent
Sparks et al.

(10) Patent No.: US 6,544,552 B2
(45) Date of Patent: Apr. 8, 2003

(54) METHOD OF PRODUCING POROUS TABLETS WITH IMPROVED DISSOLUTION PROPERTIES

(75) Inventors: Robert E. Sparks, Kirkwood, MO (US); Irwin C. Jacobs, Eureka, MO (US); Norbert S. Mason, Clayton, MO (US)

(73) Assignee: Particle and Coating Technologies, Inc., St. Louis, MO (US)

( * ) Notice: Subject to any disclaimer, the term of this patent is extended or adjusted under 35 U.S.C. 154(b) by 0 days.

(21) Appl. No.: 09/757,426

(22) Filed: Jan. 11, 2001

(65) Prior Publication Data

US 2002/0136767 A1 Sep. 26, 2002

(51) Int. Cl.$^7$ ................................................. A61K 9/20
(52) U.S. Cl. ........................ 424/464; 424/441; 424/465; 514/772.3; 514/777; 514/781; 514/951; 514/960
(58) Field of Search ................................ 424/464, 465, 424/439, 441, 489

(56) References Cited

U.S. PATENT DOCUMENTS

| | | | |
|---|---|---|---|
| 3,885,026 A | * | 5/1975 | Heinemann et al. .......... 424/14 |
| 3,951,821 A | | 4/1976 | Davidson |
| 4,134,943 A | | 1/1979 | Knitsch et al. |
| 4,305,502 A | | 12/1981 | Gregory et al. |
| 4,371,516 A | | 2/1983 | Gregory et al. |
| 4,568,547 A | | 2/1986 | Herschler |
| 4,950,484 A | | 8/1990 | Olthoff et al. |
| 5,178,868 A | | 1/1993 | Malmqvist-Granlund et al. |
| 5,202,129 A | | 4/1993 | Samejima et al. |
| 5,206,025 A | | 4/1993 | Courteille et al. |
| 5,298,261 A | | 3/1994 | Pebley et al. |
| 5,302,396 A | | 4/1994 | Phadke et al. |
| 5,501,861 A | | 3/1996 | Makino et al. |
| 5,516,530 A | | 5/1996 | Lo et al. |
| 5,529,789 A | | 6/1996 | Lo |
| 5,576,014 A | | 11/1996 | Mizumoto et al. |
| 5,720,974 A | | 2/1998 | Makino et al. |
| 5,762,961 A | | 6/1998 | Roser et al. |
| 5,776,491 A | | 7/1998 | Allen, Jr. et al. |
| 5,807,576 A | | 9/1998 | Allen, Jr. et al. |
| 5,807,577 A | | 9/1998 | Ouali |
| 5,807,578 A | | 9/1998 | Acosta-Cuello et al. |
| 5,837,285 A | | 11/1998 | Nakamichi et al. |
| 5,851,553 A | | 12/1998 | Myers et al. |
| 5,853,758 A | | 12/1998 | Lo |
| 5,869,095 A | | 2/1999 | Gergely et al. |
| 5,895,664 A | | 4/1999 | Cherukuri et al. |
| 5,935,600 A | | 8/1999 | Cherukuri et al. |
| 5,939,091 A | | 8/1999 | Eoga et al. |
| 5,955,107 A | | 9/1999 | Augello et al. |
| 5,958,453 A | | 9/1999 | Ohno et al. |
| 5,965,162 A | | 10/1999 | Fuisz et al. |

* cited by examiner

Primary Examiner—James M. Spear
(74) Attorney, Agent, or Firm—Jacobson Holman PLLC

(57) ABSTRACT

A method of producing a fast-dissolving pharmaceutical delivery device of moderate strength. The delivery device is a fully formed tablet composed of readily available sugars, strength polymers and a volatilizable excipient along with an active ingredient and optional flavorings. The tablet as made will disintegrate in an aqueous medium such as saliva in under 15 seconds, making mastication unnecessary or at least requiring only one or two bites on the tablet. Essential to the invention is the easily obtainable particle size ranges of the sugars and the volatilizable excipient which promotes optimum release and tablet strength. The invention also allows for effective taste masking of the active ingredient with standard particle coating techniques.

21 Claims, No Drawings

METHOD OF PRODUCING POROUS TABLETS WITH IMPROVED DISSOLUTION PROPERTIES

BACKGROUND OF THE INVENTION

1. Field of the Invention

The present invention is related to the field of delivery devices and, more particularly, to a method of producing rapidly dissolving pharmaceutical tablets.

2. Description of the Related Art

Many people, particularly the young and the elderly, have difficulty swallowing orally administered medications. These difficulties may arise from an inability to chew and/or swallow pills and tablets. Tablets that disintegrate rapidly, and preferably without water, are therefore highly desirable.

To achieve rapid dissolution, tablets need to be sufficiently porous. However, the tablet must also maintain its integrity prior to administration. Therefore, a need exists for a rapidly disintegrating tablet having enhanced structural integrity.

U.S. Pat. No. 4,134,943 describes a process for developing a fast dissolving tablet that requires a solvent that is inert to all components of the tablet. After mixing of all the components in the solvent, the mixture is frozen and pressed into a tablet. The solvent is then evaporated to form the porous tablet. The process is complex and quite expensive.

Another freeze drying process for forming porous tablets is described in U.S. Pat. No. 4,371,516. A gelatin or other water-soluble binder along with the pharmaceutical and acceptable sugars are all dissolved and the mixture placed in a suitable mold. The mixture is frozen and the solvent removed under vacuum. The tablets are expensive to prepare and require special packaging due to their lack of strength.

U.S. Pat. No. 5,516,530 describes an even more complex system for forming porous tablets using lyophilization. U.S. Pat. No. 5,298,261 describes a freezing process followed by vacuum drying that makes for a less porous tablet than is seen in the prior lyophilization processes.

U.S. Pat. No. 3,885,026 describes the incorporation of a readily volatilizable solid excipient into a tablet, producing a porous yet strong shape after sublimation. Dissolving times are listed at 105 to 270 seconds, which is too long for the purposes to which the present invention is directed.

A further weakness in the prior art methodologies relates to the dissolution or suspension of all components in water. When excipients as well as the active ingredients are dissolved, this precludes the use of controlled release or coated active ingredients for taste masking. More particularly, during preparation of the aqueous suspension prior to freeze drying, the coated particles can release a sufficient amount of the active ingredients to render the final tablet, after drying, unpalatable. Accordingly, a need exists for a methodology in which all dry ingredients can be used, without the need for water, so as to maintain taste masking while yet creating the requisite tablet porosity for fast dissolution.

SUMMARY OF THE INVENTION

In view of the foregoing, one object of the present invention is to overcome the difficulties that some patients encounter with orally administered medications through the production of a tablet that dissolves quickly in the mouth, allowing for effortless swallowing without any need for drinking water.

Another object of the invention is to produce a fast-dissolving tablet by optimizing component particle size ranges to promote both optimum release and tablet strength.

A further object of the invention is to produce a tablet having sufficient strength by controlling the amount of excipient within specified ranges.

A still further object of the invention is a tablet that does not require suspension of all components in water during formation and therefore allows for effective taste masking of the active ingredient.

Yet a further object of the invention is a tableting process that is cost effective, requiring only commercially available raw materials and standard tablet dies and associated machinery.

In accordance with this and other objects, the present invention is directed to a method of producing a fast-dissolving pharmaceutical delivery device of moderate strength. The formulation employed in the method utilizes at least one carbohydrate, a strengthening polymer, a volatile pore-forming excipient, and a physiologically active ingredient. By controlling and optimizing the particle size distribution ranges of the components prior to tablet formulation, particularly of the pore forming excipient, a much faster releasing tablet is obtained.

These and other objects of the invention, as well as many of the intended advantages thereof, will become more readily apparent when reference is made to the following description taken in conjunction with the accompanying examples.

DETAILED DESCRIPTION OF THE PREFERRED EMBODIMENTS

In describing a preferred embodiment of the invention, specific terminology will be resorted to for the sake of clarity. However, the invention is not intended to be limited to the specific terms so selected, and it is to be understood that each specific term includes all technical equivalents which operate in a similar manner to accomplish a similar purpose.

According to the present invention, the method of formulation utilizes one or more carbohydrates, a polymer for improving tablet strength, a volatile excipient such as ammonium bicarbonate, along with taste masking flavorings and a physiologically active ingredient. The carbohydrates may be one or more of the following examples: lactose, mannitol, sorbitol, fructose or other highly water-soluble sugar or sugar alcohol.

Particle sizes and the nature of the carbohydrate can affect both the strength and the taste of the final tablet. Lactose and sorbitol combinations are the most favorable for improving the rate of dissolution, with sorbitol concentration at approximately 10 to 35% of the pre-processed tablet mass and more specifically, 15 to 20%. Lactose concentration at 15 to 50% also proved effective, with the optimum being 30% to 40% of the pre-processed mass. Processing as defined herein is the removal by sublimation of the volatile tablet component.

Sorbitol is employed for its pleasing taste-modifying properties while the lactose is used for its superior dissolution property. Mannitol can be substituted for the lactose with only a slight decrease in disintegration time. Small amounts of maltodextrin improve the tablet strength but with the sacrifice of release time.

Sugar particle size is optimized to improve the strength and the dissolution times, with a particle size below 75 microns being desirable and, more specifically, 37 to 70 microns being optimal.

A volatile excipient such as ammonium carbonate or ammonium bicarbonate is known to create porosity in the tablet after it is heated under a vacuum for several hours. However, according to the present invention, the disintegration times of the final tablets are markedly reduced if finely ground ammonium carbonate is used. More particularly, the disintegration times as measured in a rotating basket submerged in water are greatly reduced when all of the particles of ammonium carbonate are below 70 microns in size, and preferably in the range of 37 to 70 microns. The use of even finer particles of carbonate produced only slight improvement in disintegration times.

Ammonium carbonate and ammonium bicarbonate may be used somewhat interchangeably in accordance with the present invention. Therefore, references herein to ammonium carbonate shall be understood to include the use of ammonium bicarbonate in place thereof, and vice versa. However, in practice it is noted that carbonate is preferred since water is not present during decomposition.

Controlling particle size in accordance with these ranges not only decreases the release time but increases the ultimate tablet strength. The tablet appearance is also considerably improved since there are no large pores evident on the tablet surface as occur with the use of larger particles of bicarbonate.

The smaller ammonium bicarbonate particles produce somewhat weaker tablets. Tablets made with ammonium bicarbonate sieved below 38 microns were approximately 40% weaker than those containing ammonium bicarbonate sieved below 100 microns (average size of about 60 microns). However, this reduction in strength was ameliorated, without greatly sacrificing the disintegration time, by employing ammonium bicarbonate sieved below 53 microns.

The amount of bicarbonate used in forming a tablet (pre-processed mass) also has a profound effect on disintegration, more so than its effect on tablet strength. For example, a half-inch diameter tablet with a pre-processed mass of 500 mg pressed at the same pressure showed a 40% slower release at 25% ammonium bicarbonate than a tablet containing 35% bicarbonate with the other ingredients in equal ratios. The difference in strength between the two tablets was minimal, with the 25% tablet being slightly stronger. Therefore, within a narrow range of concentration, the bicarbonate content can be increased to improve disintegration without unduly sacrificing tablet strength.

Small amounts of microcrystalline cellulose, starch, or maltodextrin can improve the strength of the tablets without significant increase in disintegration times. Particle size for these excipients was of less importance with regard to impact on the disintegration times. Approximately 2% to 8% of each of microcrystalline cellulose (for example, Avicell® of FMC) and starch (as Starch 1500, Colorcon, e.g.), more specifically 5% each, gave improved tablet strength. Small amounts of polyvinyl pyrolidone (ISP K-30), up to approximately 3%, gave improved strength without greatly affecting release times. The addition of mannitol also gave improved strength to the tablets without greatly sacrificing the dissolution behavior.

The following examples are given for the purpose of illustrating the present invention. The tablet dissolution performance was measured using a rotating basket procedure. Release times were measured by placing the tablet in a small wire basket placed on the end of a rod spinning at 100 rpm. This was placed in water and the dissolution time was noted when the tablet was completely disintegrated and there were no pieces retained by the basket screen.

EXAMPLE 1

Ammonium carbonate, microcrystalline cellulose, polyvinyl pyrolidone, mannitol and sorbitol were combined to form 400 mg of the mixture as follows:

| Ingredients | Percentage to Total |
| --- | --- |
| Ammonium carbonate | 35% |
| microcrystalline cellulose (Avicell ® 101, FMC) | 10% |
| polyvinyl pyrolidone (K-90, ISP) | 10% |
| mannitol (as received; Aldrich Chemical) | 20% |
| sorbitol (as received; Aldrich Chemical) | 25% |

The mixture was placed in a 1 cm tablet die and approximately 3000 pounds of force was applied. The tablets were then heated at 60° C. in a vacuum oven for three hours.

When ball-milled ammonium carbonate was used, the resulting tablet disintegrated completely in 5 seconds.

When ammonium carbonate as received from the supplier was used, the resulting tablet disintegrated in approximately 7 seconds.

EXAMPLE 2

Ammonium carbonate, microcrystalline cellulose, polyvinyl pyrolidone, mannitol and sorbitol were combined to form 1 gm of the mixture as follows:

| Ingredients | Percentage to Total |
| --- | --- |
| Ammonium carbonate (ground and sieved below 53 microns) | 25% |
| microcrystalline cellulose (Avicell ® 101) | 10% |
| polyvinyl pyrolidone (K-90, ISP) | 10% |
| mannitol (as received) | 35% |
| sorbitol (as received) | 20% |

The mixture was pressed in a 21 mm (0.875 inch) tablet die and approximately 2000 pounds of force was applied. The tablets were then heated under vacuum at 60° C. for three hours.

The disintegration time for the average of three tablets was just over 3 seconds.

EXAMPLE 3

Ammonium carbonate, microcrystalline cellulose, lactose, sorbitol and starch were combined to form 800 mg of the mixture as follows:

| Ingredients | Percentage to Total |
| --- | --- |
| Ammonium carbonate | 15% |
| microcrystalline cellulose | 5% |
| lactose | 50% |

-continued

| Ingredients | Percentage to Total |
|---|---|
| sorbitol | 25% |
| starch | 5% |
| (Starch 1500, Colorcon) | |

The mixture was placed in a ⅝ inch tablet die and approximately 2000 pounds of force was applied. The tablets were then heated under vacuum at 60° C. for four hours.

When the ammonium carbonate used had been ground and sieved below 53 microns, the resulting tablets disintegrated in 30 seconds.

When the ammonium carbonate was used as received (without grinding), the resulting tablets disintegrated in 42 seconds.

EXAMPLE 4

Ammonium carbonate, microcrystalline cellulose, lactose, sorbitol and starch were combined to form 800 mg of the mixture as follows:

| Ingredients | Percentage to Total |
|---|---|
| Ammonium carbonate | 25% |
| (ground and sieved below 53 microns) | |
| microcrystalline cellulose | 5% |
| lactose | 42% |
| sorbitol | 23% |
| starch | 5% |
| (Starch 1500, Colorcon) | |

The mixture was placed in a ⅝ inch tablet die and approximately 2000 pounds of force was applied. The tablets were then heated under vacuum at 60° C. for four hours.

The resulting tablets disintegrated in 13 seconds. This is faster than the tablets in example 3, in which only 15% carbonate was used, even when the ammonium carbonate had been ground and sieved below 53 microns.

EXAMPLE 5

Ammonium carbonate, microcrystalline cellulose, lactose, sorbitol and starch were combined to form 1 gm of the mixture as follows:

| Ingredients | Percentage to Total |
|---|---|
| Ammonium carbonate | 25% |
| (ground and sieved below 53 microns) | |
| microcrystalline cellulose | 5% |
| (Avicell ® 101, FMC) | |
| lactose | 40% |
| sorbitol | 25% |
| starch (Starch 1500, Colorcon) | 5% |

The mixture was pressed in a ⅝ inch tablet die and compressed. One group of tablets from this mixture was pressed at 2000 psi and another group was pressed at 2500 psi. All of the tablets were then heated in a vacuum oven at 65° C. for four hours.

The tablets pressed at the lower pressure disintegrated in 13 seconds, while those pressed at the higher pressure disintegrated in 26 seconds.

EXAMPLE 6

Ammonium carbonate, microcrystalline cellulose, mannitol, sorbitol and starch were combined to form 800 mg of the mixture as follows:

| Ingredients | Percentage to Total |
|---|---|
| Ammonium carbonate | 25% |
| (ground and sieved below 53 microns) | |
| microcrystalline cellulose | 5% |
| (Avicell ® 101, FMC) | |
| mannitol granules | 40% |
| (SD200, Roquette America) | |
| sorbitol | 25% |
| starch (Starch 1500, Colorcon) | 5% |

A mixture of the mannitol, sorbitol, and starch was granulated in a small planetary drive mixer by the addition of atomized water on the mixture as it was mixing. After drying, the granules were mixed with the carbonate and microcrystalline cellulose, and 800 mg of the mixture was pressed in a ⅝ inch tablet die and compressed at 2000 psi. The tablets were then heated in a vacuum oven at 60° C. for four hours.

The disintegration time was approximately 10 seconds.

The foregoing descriptions and drawings should be considered as illustrative only of the principles of the invention. The invention may be configured in a variety of shapes and sizes and is not limited by the dimensions of the preferred embodiment. Numerous applications of the present invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

What is claimed is:

1. A process for producing a porous, rapidly dissolving, tablet comprising providing a quantity of a decomposable excipient selected from the group consisting of ammonium carbonate and ammonium bicarbonate having a range of particle sizes, some of which exceed 70 microns, separating from said quantity of said excipient a fraction having a particle size below about 70 microns, dry mixing said fraction of said excipient with other tablet components, forming said mixture into a tablet, and then heating said tablet at a temperature and pressure for sufficient time to decompose and remove said excipient and thereby form pores in said tablet.

2. The process of claim 1 wherein said excipient is ground and sieved to produce said fraction having a particle size below about 70 microns.

3. The process of claim 1 wherein said other tablet components include at least one carbohydrate, at least one strengthening ingredient, and a physiologically effective amount of a pharmaceutical material.

4. A porous delivery device comprising:
    about 35% ammonium carbonate, ground and sieved below 53 microns;
    about 10% microcrystalline cellulose;
    about 10% polyvinyl pyrolidone;
    about 20% mannitol; and
    about 25% sorbitol.

5. In the production of a porous, rapidly dissolving tablet wherein the tablet components are mixed and pressed into a shape, the improvement comprising the incorporation into the mix of approximately 35% ammonium carbonate or ammonium bicarbonate that has been ground and sieved below 70 microns, approximately 10% microcrystalline cellulose, approximately 10% polyvinyl pyrolidone, approximately 20% mannitol, and approximately 25% sorbitol, and thereafter pressing the mix into a tablet die and then heating at a temperature of about 60° C. under vacuum for approximately three hours, whereby the resulting tablets are porous, strong and readily disintegratable.

6. The process according to claim 5, wherein the ammonium carbonate or ammonium bicarbonate is sieved below 53 microns.

7. The process according to claim 5, wherein the ammonium carbonate or ammonium bicarbonate is sieved to yield particles about 37–70 microns.

8. The process according to claim 5, wherein the mix is pressed into said tablet die with approximately 2000 psi.

9. In the production of a porous, rapidly dissolving tablet wherein the tablet components are mixed and pressed into a shape, the improvement which comprises the process of incorporating into the mix approximately 25% ammonium carbonate or ammonium bicarbonate that has been ground and sieved below 70 microns, approximately 5% microcrystalline cellulose, approximately 42% lactose, approximately 23% sorbitol, and approximately 5% starch, and thereafter pressing the mix into a tablet die and then heating at a temperature of about 60° C. under vacuum for approximately four hours, whereby the resulting tablets are porous, strong and readily disintegratable.

10. The process according to claim 9, wherein the ammonium carbonate or ammonium bicarbonate is sieved below 53 microns.

11. The process according to claim 9, wherein the ammonium carbonate or ammonium bicarbonate is sieved to yield particles about 37–70 microns.

12. The process according to claim 9, wherein the mix is pressed into said tablet die with approximately 2000 psi.

13. In the production of pharmaceutical tablets from a mix of ingredients including at least one carbohydrate, a polymer for improving tablet strength, a volatile excipient, and a physiologically active ingredient, which tablets are to undergo disintegration in use, the improvement which comprises the volatile excipient being at least 25% of the mix and having a particle size of less than 70 microns.

14. The improvement according to claim 13, wherein the volatile excipient is 35% of the mix.

15. The improvement according to claim 13, wherein the volatile excipient is ammonium carbonate sieved below about 37–70 microns.

16. The improvement according to claim 13, wherein the volatile excipient is ammonium carbonate sieved below 53 microns.

17. The improvement according to claim 14, wherein the volatile excipient is ammonium carbonate sieved below about 37–70 microns.

18. The improvement according to claim 14, wherein the volatile excipient is ammonium carbonate sieved below 53 microns.

19. The improvement according to claim 13, wherein the polymer for improving tablet strength includes mannitol granules and is approximately 40% of the mix.

20. The process of claim 3 wherein said carbohydrate is selected from the group consisting of lactose, mannitol, sorbitol, fructose and mixtures thereof.

21. The process of claim 3 wherein said strengthening ingredient is selected from the group consisting of microcrystalline cellulose, starch, maltodextrin, polyvinyl pyrolidone and mixtures thereof.

* * * * *